(12) United States Patent
Theiner et al.

(10) Patent No.: US 11,473,034 B2
(45) Date of Patent: Oct. 18, 2022

(54) HIGHLY STABLE AND ALKALINE CLEANING SOLUTIONS AND SOLUBLE SURFACTANT

(71) Applicant: EVONIK OPERATIONS GMBH, Essen (DE)

(72) Inventors: Eric Theiner, Midlothian, VA (US); Buford Brian Smith, Evansville, WI (US); Khalil Yacoub, Allentown, PA (US); Larry Meyers, Milton, WI (US)

(73) Assignee: Evonik Operations GmbH, Essen (DE)

( * ) Notice: Subject to any disclaimer, the term of this patent is extended or adjusted under 35 U.S.C. 154(b) by 64 days.

(21) Appl. No.: 16/967,099

(22) PCT Filed: Feb. 5, 2019

(86) PCT No.: PCT/EP2019/052756
§ 371 (c)(1),
(2) Date: Aug. 3, 2020

(87) PCT Pub. No.: WO2019/154797
PCT Pub. Date: Aug. 15, 2019

(65) Prior Publication Data
US 2021/0163847 A1    Jun. 3, 2021

(30) Foreign Application Priority Data
Feb. 6, 2018 (EP) .................... 18155322

(51) Int. Cl.
*C11D 3/02* (2006.01)
*C11D 3/30* (2006.01)
(Continued)

(52) U.S. Cl.
CPC .......... *C11D 1/10* (2013.01); *C11D 1/72* (2013.01); *C11D 1/722* (2013.01); *C11D 1/88* (2013.01);
(Continued)

(58) Field of Classification Search
CPC .. C11D 1/72; C11D 1/722; C11D 1/88; C11D 1/94; C11D 3/08; C11D 3/10; C11D 3/044; C11D 3/26; C11D 3/30
(Continued)

(56) References Cited

U.S. PATENT DOCUMENTS

| 4,416,792 A | 11/1983 | Blackstone |
| 4,878,951 A | 11/1989 | Pochard et al. |

(Continued)

FOREIGN PATENT DOCUMENTS

| CN | 1311813 | 9/2001 |
| EP | 0 213 054 | 3/1987 |
| EP | 0 263 911 | 4/1988 |

OTHER PUBLICATIONS

International Preliminary Report on Patentability for corresponding international application PCT/EP2019/052756, filed Feb. 5, 2019.
(Continued)

*Primary Examiner* — Gregory R Delcotto
(74) *Attorney, Agent, or Firm* — Law Office of Michael A. Sanzo, LLC (57) ABSTRACT

The present invention relates to new alkaline, preferably highly alkaline, cleaning solutions comprising surfactants with improved stability and cleaning performance under such conditions. It further relates to novel surfactants.

19 Claims, 2 Drawing Sheets

TICs for the LC-ESI (+) MS analyses of un-aged (top) and aged (bottom) Monosodium Cyclohexylamine Dipropionate at a cone voltage of 15 V.

(51) Int. Cl.

| | | |
|---|---|---|
| C11D 7/10 | (2006.01) | |
| C11D 7/32 | (2006.01) | |
| C11D 1/10 | (2006.01) | |
| C11D 3/00 | (2006.01) | |
| C11D 3/04 | (2006.01) | |
| C11D 3/12 | (2006.01) | |
| C11D 11/00 | (2006.01) | |
| C11D 17/00 | (2006.01) | |
| C11D 1/88 | (2006.01) | |
| C11D 1/94 | (2006.01) | |
| C11D 1/72 | (2006.01) | |
| C11D 1/722 | (2006.01) | |
| C11D 3/08 | (2006.01) | |
| C11D 3/10 | (2006.01) | |
| C11D 3/26 | (2006.01) | |

(52) U.S. Cl.
CPC .............. *C11D 1/94* (2013.01); *C11D 3/0047* (2013.01); *C11D 3/044* (2013.01); *C11D 3/08* (2013.01); *C11D 3/10* (2013.01); *C11D 3/1226* (2013.01); *C11D 3/1233* (2013.01); *C11D 3/1246* (2013.01); *C11D 3/26* (2013.01); *C11D 3/30* (2013.01); *C11D 11/0023* (2013.01); *C11D 17/0013* (2013.01)

(58) Field of Classification Search
USPC ....... 510/422, 434, 477, 488, 499, 505, 506, 510/509, 511
See application file for complete search history.

(56) References Cited

U.S. PATENT DOCUMENTS

| | | | |
|---|---|---|---|
| 4,913,841 A | 4/1990 | Zeman | |
| 4,935,065 A | 6/1990 | Bull | |
| 4,975,216 A | 12/1990 | Schluessler | |
| 5,015,412 A | 5/1991 | Zeman | |
| 5,189,067 A | 2/1993 | Klimisch et al. | |
| 5,192,461 A | 3/1993 | Tomaszewski et al. | |
| 5,380,468 A | 1/1995 | Gober et al. | |
| 5,730,791 A | 3/1998 | Krogh et al. | |
| 5,929,007 A | 7/1999 | Feng | |
| 5,972,875 A | 10/1999 | Crutcher et al. | |
| 6,080,713 A | 6/2000 | Crutcher | |
| 6,146,427 A | 11/2000 | Crutcher | |
| 6,169,064 B1 | 1/2001 | Krogh et al. | |
| 6,191,099 B1 | 2/2001 | Crutcher | |
| 6,221,834 B1 * | 4/2001 | Yamamoto | C11D 3/2086 510/480 |
| 6,277,801 B1 | 8/2001 | Dahanayake et al. | |
| 6,506,261 B1 | 1/2003 | Man | |
| 6,530,383 B1 | 3/2003 | Rogmann et al. | |
| 6,537,960 B1 | 3/2003 | Ruhr et al. | |
| 6,555,511 B2 | 4/2003 | Renfrow | |
| 6,589,926 B1 | 7/2003 | Vinson et al. | |
| 7,008,911 B2 | 3/2006 | Griese et al. | |
| 7,572,761 B2 | 8/2009 | Gefvert | |
| 7,868,208 B1 | 1/2011 | O'Lenick et al. | |
| 8,216,989 B2 | 7/2012 | Silvernail et al. | |
| 8,460,477 B2 | 6/2013 | Hodge et al. | |
| 2004/0235982 A1 | 11/2004 | Rabasco et al. | |
| 2007/0036832 A1 | 2/2007 | Williams et al. | |
| 2009/0088565 A1 | 4/2009 | Schick et al. | |
| 2009/0249975 A1 | 10/2009 | Herschke | |
| 2010/0009892 A1 | 1/2010 | Hauke et al. | |
| 2012/0142577 A1 * | 6/2012 | Sun | B01F 17/0085 510/479 |
| 2015/0291914 A1 | 10/2015 | Sun et al. | |

OTHER PUBLICATIONS

International Search Report for corresponding international application PCT/EP2019/052756, filed Feb. 5, 2019.
Written Opinion of the International Searching Authority for corresponding international application PCT/EP2019/052756, filed Feb. 5, 2019.
Amaral, et al., "Foamability of Detergent Solutions Prepared with Different Types of Surfactants and Waters," *Journal of Surfactants and Detergents* 11(4):275-278 (Dec. 2008).
Preston, "Some correlating principles of detergent action," *J. Phys. Colloid Chem*, 52(1):84-96 (Jan. 1948).

* cited by examiner

HIGHLY STABLE AND ALKALINE CLEANING SOLUTIONS AND SOLUBLE SURFACTANT

CROSS REFERENCE TO RELATED APPLICATIONS

The present application is US national stage of international application PCT/EP2019/052756, which had an international filing date of Feb. 5, 2019, and which was published on Aug. 15, 2019. The PCT application claims priority to EP 18155322.3, filed on Feb. 6, 2018, which is hereby incorporated by reference in its entirety.

The present invention relates to new alkaline, preferably highly alkaline, cleaning solutions comprising surfactants with improved stability and cleaning performance under such conditions. It further relates to novel surfactants.

Highly alkaline, or "heavily built," cleaning solutions have become a mainstay in a number of niche and general application areas because of the benefit of using alkaline materials in cleaning processes. For example, meat and poultry processing plants will employ such solutions in cleaning because of the action of strong alkali in breaking down the physical and chemical structure of fats left behind on food processing equipment as soil. The alkaline material will interact with the physical fat structure to allow the soil to be removed more easily by mechanical action as well as reacting chemically with the triglycerides that comprise fatty soils. The alkaline materials will further aid in soil removal by dispersing the removed soil and limiting the ability of such soils to redeposit on the cleaned surfaces. In a similar way, such solutions may be brought to bear as drain cleaners to break down the water-insoluble organic deposits that will result in a clogged or slow drain. The action of such alkaline solutions is not limited solely to organic soils, as these materials may also be used to leach mineral components to aid in the removal of ceramic or similar mineral deposits from surfaces.

To improve the effectiveness and speed of alkaline cleaning solutions additives are generally employed, the most important of which, it may be argued, are surface active agents, or surfactants. Surfactants are materials that are comprised of hydrophilic and hydrophobic regions that result in properties unique to this class of material, particularly having a free energy drive to migrate to interfaces and form aggregate structures commonly referred to as micelles. The interfacial activity speeds the process of wetting and penetration of the soil by the cleaning solution and the micellar structures aid in the emulsification and dispersion of removed soils.

Because of their surface activity, surfactants will often contribute significantly to foaming. This may be beneficial for some applications as foam can allow a small amount of solution to be distributed easily across a large area and cling to surfaces for an extended time, but other applications that employ vigorous agitation such as recirculating clean-in-place (CIP) systems are negatively impacted by foam. For this reason, it is important to be cognizant of the foaming properties of a solution and to employ the proper surfactant to produce the desired level of foam.

Incorporating an effective surfactant in a built solution often presents a challenge. Surfactants are solubilized in solution via hydrogen bonding between the hydrophilic portion of the surfactant and the water of the solution. Water will also preferentially form a hydration radius around alkaline builders producing a relative scarcity of water to interact with the surfactant hydrophile. Without the free interaction between the hydrophile and water, the surfactant aggregates will potentially become crystalline and, with decreasing water availability, insoluble. Nevertheless, there is a need in the market for built and highly built cleaning solutions and new surfactants are needed that remain soluble even in highly built cleaning formulations.

Furthermore, some surfactants are open to nucleophilic attack on the part of the hydroxyl ion ($OH^-$) present in alkaline solutions. This reaction may destroy the functionality of the surfactant by changing its chemical structure. This is of particular concern at elevated temperatures because of the increased activity of chemical systems at higher temperatures. Elevated temperatures are often used in cleaning operations to aid and speed the removal of soil, so high temperature stability on the part of surfactants is to be desired. Thus, new surfactants are needed that maintain their molecular integrity even in highly built cleaning formulations.

Various techniques and co-ingredients are employed in the prior art in order to allow the solution of a surfactant into the built formula. One such method is to employ a surfactant with a very high solubility, either to act as the primary surfactant or to provide a solubilizing effect known as "hydrotroping." Many such surfactants are not particularly effective as dynamic wetting agents or detergents owing to structural considerations endemic to their design. Furthermore, incorporating a hydrotroping surfactant to allow the use of a more effective detergent will increase the overall cost of the cleaning formula.

As consequence of the problems described before, there has been considerable interest in developing surfactants with effective detergency that will be soluble in highly built systems. For example prior art indicates the use of dialkyl diphenyloxide disulfonate, alkyl polyglucoside, alkyl amine oxide, alkyl phosphate ester, and sulfobetaine amphoteric surfactants. Also of note in prior art is the use of alkyl dipropionate surfactants utilizing hydrophobe size in the typical detergent range (e.g. >$C_7$). Reference is made to EP 0 213 054 B1, EP 0 263 911A1, U.S. Pat. No. 4,878,951 B1, U.S. Pat. No. 4,913,841 B1, U.S. Pat. No. 4,935,065 B1, U.S. Pat. No. 4,975,216 B1, U.S. Pat. No. 5,015,412 B1, U.S. Pat. No. 5,192,461 B1, U.S. Pat. No. 5,380,468 B1, U.S. Pat. No. 5,929,007 B1, U.S. Pat. No. 6,277,801 B1, U.S. Pat. No. 6,506,261 B1, U.S. Pat. No. 6,530,383 B1, U.S. Pat. No. 6,537,960 B1, U.S. Pat. No. 6,555,511 B1, U.S. Pat. No. 7,008,911 B1, U.S. Pat. No. 8,216,989 B1, U.S. Pat. No. 8,460,477, US 2007/0036832 A1, US 2010/0009892 A1.

U.S. Pat. No. 4,416,792 describes the use of iminodipropionates as processing aid to prevent or to minimize the separation of nonionic surfactants in a detergent slurry mixture and to stabilize such slurry before it is used in a tower spray drying process to produce spray-dried detergent formulations. No hint is found in U.S. Pat. No. 4,416,792 that iminodipropionates can be used to solve the problems of built or highly built cleaning solutions discussed before.

Even though progress has been made during the years, there remains an ongoing need for effective cleaning solutions that will incorporate a high level of alkaline builders, remain stable over time in concentrated form, and will provide a desired level of foaming in conjunction with the method of use. And there is an ongoing need for improved surfactants capable of use in such cleaning solutions.

The object of the present therefore was to provide new surfactants and new cleaning solutions not having the problems described before for the prior art formulations or having those only to a reduced extent.

A special object of the present invention was to provide a new surfactant capable of maintaining solubility in built or heavily built solutions that provide effective wetting and detergency and that maintains molecular integrity under such conditions so that it is not broken down or chemically changed by the built cleaning solution. In a special object of the present invention the new surfactant should have high solubility and keep its molecular integrity even under application at high temperatures, preferably at temperatures above 100° C., more preferred at temperatures of 120 to 180° C., even more preferred at temperatures of 140 to 160° C.

It is also an object of the present invention to provide new surfactants and new built or highly built cleaning solutions, preferably with a high alkalinity content, which are stable without hydrotroping and thus, have relatively low costs.

A further special object of the present invention was to provide a new surfactant with improved foaming properties that allows one to obtain cleaning solutions with a desired degree of foaming.

Further objects not explicitly stated here become obvious in the overall context of the description, examples, figures and claims of the present invention.

The inventors found out that the problems described above can be solved by cleaning solutions comprising surfactants containing compact hydrophobic and hydrophilic functional groups. The compact structure ensures that speed of migration is maintained and aids in solubility of the surfactant in order to maintain solubility in a built solution over time. In contrast thereto, surfactants used in the prior art, having larger structures, begin to lose dynamic surface activity when diffusion is hindered by the electrolyte present in built or highly built formulations.

The surfactants of the present invention can be incorporated into a high level of alkaline builders even in high concentrations. Cleaning solutions of the present invention remain stable over time, even in concentrated form and can provide a desired level of foaming in conjunction with the method of use. They provide effective detergency, shelf stability, and extended service life under extreme conditions.

As consequence of the foresaid, cleaning solutions as claimed in claim 1 and surfactants as claimed in claim 12 are embodiments of the present invention. Preferred embodiments are claimed in the dependent claims and are described in more detail in the following description and examples.

Before describing the invention in detail, some frequently used terms are defined.

"Compact" in the sense of the present invention means that the alkyl spacers between the functional groups have maximum four carbon atoms. Alkyl radicals as end chain have a maximum of seven, preferably of six or 3 to 5 carbon atoms. The alkyl portion, or hydrophobe, is therefore more compact than a traditional surfactant used to enhance detergency or wetting.

The terms "cleaning solution", "cleaning composition" and "cleaning formulation" are used synonymously in the present invention. "Solution" means that all components are dissolved in water, which differentiates solutions from emulsions, dispersions and slurries.

To simplify comparison of levels of alkalinity, the degree of total alkalinity in the present invention is, unless otherwise explicitly stated, expressed as "weight percentage of equivalent $Na_2O$ in the cleaning solution". In this way a solution of 50 wt. % sodium hydroxide (NaOH) is expressed has having an alkaline content, or total alkalinity, of 38.0 wt. % $Na_2O$ and a 20 wt. % solution of sodium carbonate ($Na_2CO_3$) is said to have a total alkalinity of 11.6 wt. % $Na_2O$.

Solutions with relatively high levels of total alkalinity (e.g. >1.5 wt. %, in particular >5 wt. % $Na_2O$) are referred to as "built," and a formula with exceptionally high levels of builders (e.g. >10 wt. %, in particular >15 wt. % $Na_2O$) are referred to as "heavily built."

Materials used to obtain alkaline cleaning solutions are referred to as "detergent builders," "alkaline builders," or simply "builders."

Some embodiments of the present invention are illustrated as an example and are not limited by the structures of the accompanying drawings, in which like references may indicate similar elements.

In one embodiment the present invention is directed to cleaning solutions comprising
a) one or more surfactant(s) according to Formula (I)

$$R_1-(O-R_2)_m-N\begin{pmatrix}(R_5)-COX_1\\|\\|\\(R_6)-COX_3\end{pmatrix}-(R_3-N)_n-(R_4)-COX_2 \quad \text{Formula (I)}$$

wherein
$R_1$ is a linear, branched, or cyclic, saturated or unsaturated aliphatic group having from 3 to 7, preferred 3 to 6, more preferred 4 to 6 and most preferred 3 to 5 or 6 carbon atoms or an aryl group having 6 or 7 carbon atoms or an alkylaryl group having 7 carbon atoms, and
$R_2$ and $R_3$ may be identical or different and are bivalent alkyl radicals with two to four carbon atoms, preferably selected from the group consisting of n-propyl group and isopropyl group, and
$R_4$, $R_5$, and $R_6$ may all be identical or two of them may be identical or all may be different and are selected from the group consisting of an ethyl group, n-propyl group, isopropyl group, n-butyl group, isobutyl group, or tert-butyl group, preferably ethyl, iso-propyl or n-propyl, most preferred ethyl, and
$X_1$, $X_2$ and $X_3$ may all be identical or two of them may be identical or all may be different and are selected from the group consisting of OH and $O^-Y^+$, wherein $Y^+$ is a cation, and
m is 0 or 1, n is 0, 1, 2 or 3, preferably 0, 1 or 2, most preferred 0 or 1, with the exception that n is 1, 2 or 3, preferably 1 or 2, most preferred 1, if m=0 and if $R_1$ comprises a tertiary carbon atom attached to the nitrogen atom,
b) one or more alkaline compound(s)
c) water.

In a further embodiment the present invention is directed to new surfactants according to Formula (I), wherein $R_1$ to $R_6$, $X_1$ to $X_3$, m and n are defined as above, and
wherein n is 1, 2 or 3, preferably 1 or 2, most preferred 1, if m=0 and if $R_1$ comprises a tertiary carbon atom attached to the nitrogen atom, and
wherein $R_1$ is selected from the group consisting of a linear saturated aliphatic group having from 3 to 5, preferably 3 or 4 carbon atoms, a linear unsaturated aliphatic group having from 3 to 7, preferably 3 to 6, most preferred 6 carbon atoms, a branched or cyclic, saturated or unsaturated aliphatic group having from 3 to 7, preferably 3 to 6, most preferred 6 carbon atoms, an aryl group having 6 or 7 carbon atoms and an alkylaryl group having 7 carbon atoms, if n=0 and if m=0 or 1.

Both conditions mentioned above regarding the combinations of $R_1$, m and n have to be fulfilled simultaneously, i.e. tert-butyl may not be selected as $R_1$ if n=0 and m=0. However, it may be selected if n=1 to 3 and m=0 or if m=1 and n=0 to 3.

Preferred alternatives for all embodiments of the invention will be described below.

The cation $Y^+$ is preferably the positively charged ion of an organic or inorganic base. Preferably the base is present in sufficient amount to neutralize one half of the acid functions present. However, the base may be present in amounts excess of the amount required to neutralize a single acid function, for example about 1 to 2 molar equivalents of base per mole of acid functions present. Preferred cations $Y^+$ are $Na^+$, $K^+$, $Li^+$, or $H^+$.

The surfactant of the invention, according to Formula (I) preferably comprises alkyl aminopropionate functionalities, derivatives thereof, or mixtures thereof.

Also preferred the surfactant according to Formula (I) comprises an amine propionate or an ether amine propionate, or mixtures thereof. Thus, preferably $R_4$ and/or $R_5$ and/or $R_6$ is/are ethyl, n-propyl or isopropyl, most preferred ethyl.

Also preferred the hydrophobe of the surfactant is comprised of an alkyl amine, an aryl amine, an alkyl or aryl ether amine, and all potential isomers of said amines, with the hydrophobe having a maximum of seven carbon atoms, preferably a maximum of six carbon atoms.

Further particular preferred embodiments are characterized as follows:

$R_4$ and $R_6$ might be identical or different and are selected from the group consisting of ethyl, n-propyl, or isopropyl, most preferred ethyl, $R_1$=cyclohexyl, m=0 and n is 0 or 1, $R_3$ if present is n-propyl or isopropyl, $R_5$ if present is ethyl, n-propyl, or isopropyl, most preferred ethyl, $X_2$, $X_3$ and if present $X_1$ are defined as above, $R_4$ and $R_6$ might be identical or different and are selected from the group consisting of, most preferred ethyl, $R_1$=butyl, m=1 and n=0 or 1, $R_2$=n-propyl or isopropyl, $R_3$ if present is n-propyl or isopropyl, $R_5$ if present is ethyl, n-propyl, or isopropyl, most preferred ethyl, $X_2$, $X_3$ and if present $X_1$ are defined as above, $R_4$ and $R_6$ might be identical or different and are selected from the group consisting of, most preferred ethyl, $R_1$=2-ethylpentyl, m=1, n is 0 or 1, $R_2$=n-propyl or isopropyl, $R_3$ if present is n-propyl or isopropyl, $R_5$ if present is ethyl, n-propyl, or isopropyl, most preferred ethyl, $X_2$, $X_3$ and if present $X_1$ are defined as above.

The surfactants according to Formula (I) with n and m=0 can for example be obtained by reacting a $C_3$ to $C_7$ linear, branched, or cyclic, saturated or unsaturated aliphatic amine or an alkylaryl amine or an aryl amine with for example two acrylic acid or methacrylic acid equivalents, followed, if necessary by neutralisation to obtain mono- or di salts.

The surfactants according to Formula (I) with m=1 can for example be obtained by reacting a $C_3$ to $C_7$ linear, branched, or cyclic, saturated or unsaturated aliphatic alcohol or an alkylaryl alcohol with for example acrylonitrile, followed by reduction to the corresponding primary amine and reaction of said primary amine with two acrylic acid or methacrylic acid equivalents, followed, if necessary by neutralisation to obtain mono- or di salts.

Further, alternative synthesis routs can easily be found by one skilled in the art.

With regard to the cleaning solution of the invention, the amount of the surfactant a) necessary in a particular cleaning solution can be determined by measuring the critical micelle concentration, the value of which represents the lowest possible concentration of a surfactant in a given solution at which it would be expected to be effective.

There may be more than one component according to Formula (I) and/or other surfactants present in the composition. The amount and types of other constituents in the composition will impact the critical micelle concentration significantly. Preferably, however, the sum of all surfactant(s) including surfactant(s) a) present in the composition should be at a concentration of 0.01-5 wt. % of the overall cleaning composition, in particular at the point of use. More preferred they should be present in sum in a concentration of 0.1-2 wt. % of the overall cleaning composition. Particular preferred the content of components a) having a structure according to Formula (I), with $R_1$ to $R_6$, $X_1$ to $X_3$, n and m being defined as above, in sum is 0.01 to 5 wt. %, preferably 0.1 to 2 wt. %, most preferred 2 wt. % of the overall cleaning composition. These concentrations ensure a positive impact on soil penetration and surface wetting and are valid for the preferred embodiments described further below, too. It was surprising that highly built cleaning formulations with highly soluble surfactants show good cleaning properties at such low surfactant concentrations.

As mentioned before, cleaning compositions of the present invention may comprise mixtures of surfactants according to Formula (I) in any combination. It may also include a mixture of one or more surfactants according to Formula (I) with other amine carboxylates.

Further surfactants, having a structure different from Formula (I), may be employed to augment the wetting and penetration properties of the present invention. Such surfactants may be nonionic, cationic, or anionic, as known to one skilled in the art.

A particular advantage of the cleaning compositions of the present invention, however, is that the required amount of non-ionic surfactants is very low, respectively it is possible to abstain from using non-ionic surfactants. Thus, it is preferred, that the cleaning compositions of the present invention comprise nonionic surfactants in a maximum amount of 0.5 wt. % of the overall cleaning composition, preferably 0.0001 wt. % to 0.3 wt. %, more preferred 0.001 wt. % to 0.2 wt. %, even more preferred 0.001 wt. % to 0.1 wt. %, of the overall cleaning composition, most preferred does not comprise any nonionic surfactants.

The alkaline component b) of the cleaning solution of the present invention may be generally selected from any type of alkaline builder. Any kind of base can be added to the solution. Preferably strong bases, i.e. bases having a pKb value at 25° C. and 1 atm of below 1, weak bases, i.e. bases having a pKb value at 25° C. and 1 atm of from 1 to 7, and/or alkaline salts to provide the desired total alkalinity are used.

It is preferred that the alkaline material be selected from the group consisting of metal hydroxides, alkaline silicates, alkaline phosphates, amines, organic chelating agents, and mixtures and combinations of these compounds.

As indicated before, the amount of base component b) in the cleaning solution will vary, depending upon the cleaning application and the nature of the soil being removed.

In a first preferred embodiment of the present invention the amount of base used will produce a total alkalinity of 10-40 wt. %, preferably 10 to 35 wt. % and more preferred 15 to 30 wt. %, expressed as $Na_2O$. Such heavily built formulas are provided to both industrial and consumer cleaning markets. Cleaning compositions for use in these markets are typically formulated using different alkaline constituents. Industrial-market compositions preferably comprise a mixture of water, strong base, chelating agents and/or dispersants, and surfactants. The surfactant constituent is provided to wet the soiled substrate and soil to allow the other formula constituents to interact with the soil by reducing interfacial tension as well as to help disperse removed soils and aid in the prevention of soil redeposition on cleaned surfaces.

The high level of total alkalinity in the cleaning solutions of the present invention provides a soil removing effect through physical and chemical interaction of fats, greases, and oils. The amount of total alkalinity will depend largely upon the nature of the facility or apparatus being cleaned and the amount of soil needing to be removed.

If strong base is used as component b) in this first preferred embodiment, sodium hydroxide or potassium hydroxide or mixtures thereof are preferably used.

Also preferred an alkaline silicate may be added as component b) to contribute to the high total alkalinity and in addition to provide a cleaning benefit as well as to provide corrosion inhibition to metal surfaces. Any silicate that dissolves to provide silica ($SiO_2$) and alkali ($Y_2O$) radicals, wherein Y is an alkali metal, preferably potassium or sodium, is suitable for this purpose. The amount to be used will preferably not exceed 15 wt. % of the overall formulation. In higher concentrations, silicates may cause problems with solubility and formula stability.

Preferred applications of such highly built compositions are for removing heavy fats and greases that make up many soils in food and beverage processing plants, in particular in an industrial food processing plant, slaughterhouse, rendering plant, dairy, or brewery.

In a second preferred embodiment the amount of base used will produce a total alkalinity of equal to or greater than 1.5 wt. %, preferably equal to or greater than 5 wt. % expressed as $Na_2O$, preferably 5 to 10 wt. %.

Consumer-market built cleaning formulas commonly utilize a lower level of strong base, if any. These cleaning compositions are typically comprised of alkaline silicates, weak bases, chelating agents and/or dispersants, and surfactants. Aesthetic additives such as fragrance and/or dye may be included as well.

The amount of alkalinity in this second preferred embodiment will depend largely upon the nature of the facility or apparatus being cleaned and the amount of soil needing to be removed. The alkaline component of the cleaning solution of the present invention may be generally selected from any type of alkaline builder. Alkaline material may be selected from the group consisting of metal hydroxides, metal carbonates, alkaline silicates, alkaline phosphates, amines, organic chelating agents, and mixtures and combinations thereof. Preferably, the alkaline material is a weak base such as sodium or potassium carbonate, alkaline, preferably sodium or potassium, silicate, the hydrates of alkaline, preferably sodium or potassium, silicate, organic alkaline materials, or mixtures thereof.

The amount of base component in the cleaning solution will vary, depending upon the cleaning application and the nature of the soil being removed. Typically, the amount of base, preferably the aforementioned weak bases, if used will produce a total alkalinity of 1.5-10.0 wt. %, preferably 5-10.0 wt. %, of the overall composition expressed as $Na_2O$. This is because consumer products are preferably less alkaline for perceived safety and because it is very difficult to get higher levels because of the concentration of the salts required.

Alkaline silicate may be added to provide a cleaning benefit as well as to provide corrosion inhibition to metal surfaces. Any alkaline silicate that dissolves to provide silica ($SiO_2$) and alkali ($Y_2O$) radicals, wherein Y is an alkali metal, preferably potassium or sodium, is suitable for this purpose. The amount to be used will typically not exceed 10 wt. % of the overall composition. In addition to solubility and stability concerns noted above, high levels of silicates also contribute alkalinity and that is preferably lowered for consumer applications as explained before.

Such built compositions are preferably used for consumer cleaning markets but may also be used in industrial cleaning composition. Preferred applications are cleaning ovens, grills, drains, ventilation hoods, stove tops, and baking pans.

Beside components a) to c) described before, the cleaning solution of the present invention may further comprise chelating agents and preferably mineral, dispersants. Typical chelating agents used in built cleaning solutions are preferably strong and multi-valent chelating agents. These include, but are not limited to phosphates, carboxylates, phosphonates, and polyphosphates. The most preferred chelating agents are the aminocarboxylates such as nitrotriacetic acid (NTA), ethylenediaminetetraacetic acid (EDTA), diethylenetriaminepentaacetic acid (DTPA), glutamic acid diacetic acid (GLDA), and methylglycinediacetic acid (MGDA). Typical mineral dispersants include, but are not limited to alkali metal salts of polyacrylic acid and polyacrylic/maleic acid copolymers.

Other additives may also be added to the cleaning solution of the present invention, including products such as emulsifiers, biocides, corrosion inhibitors, dyes, foam control agents, and other similar products known to those skilled in the art.

In general, the cleaning compositions of the present invention are suitable for all kind of applications where fats and greases have to be removed. Exemplary cleaning formulas would be used in a broad range of applications, including, but not limited to, use in cleaning fatty or greasy soils from food and/or beverage processing equipment. They may further be used as drain cleaner, kitchen cleaner, to leach mineral components, to remove ceramic or mineral deposits from surfaces, to remove paint, and to aid in graffiti removal.

It is understood that variations may be made in the foregoing without departing from the scope of the invention.

Analytical Methods

Determination of Critical Micelle Concentration (CMC)

CMC is the characteristic concentration of surface active agents (surfactants) in solution above which the appearance and development of micelles coincides with sudden variation in the relationship between the concentration and certain physico-chemical properties of the solution (such as the surface tension). Above the CMC the concentration of singly dispersed surfactant molecules is virtually constant and the surfactant is at essentially its optimum of activity for many applications. All tests were conducted in duplicate, by standard surface tension as a function of concentration experimentation using a Kruss K12 Tensiometer to measure multiple concentrations of surfactant in the solution of interest. The concentration at which the surface tension attains the lowest value consistent with increasing concentrations is determined to be the CMC. This method is well documented elsewhere in scientific literature, such as Preston, W. C., "Some correlating principles of detergent action", J. Phys. Colloid Chem., 52, 84-96 (1948).

Determining Total Alkalinity of the Cleaning Composition

Alkaline content of a solution may be determined either by using a weighted average of percent alkalinity of the solution components or by direct measurement via titration. In the case of the former, values expressing alkalinity as weight percent $Na_2O$ may be found in a number of sources, such as Kanegsberg, B and Kanegsberg, E, Handbook for Critical Cleaning ($2^{nd}$ Ed.). Boca Raton: CRC Press, 2011.

Direct measurement of the alkalinity of a solution may be made by titrating the solution with a standardized acid. While the active alkalinity is considered to be the amount of alkalinity neutralized to obtain a phenolphthalein indicator endpoint (or a pH of 8.2), the total alkalinity is considered to be the amount of alkalinity neutralized to obtain a methyl orange endpoint (or a pH of 4.4). A more detailed description may be found in sources such as Milwidsky, B M and Gabriel, D M, Detergent Analysis, A Handbook for Cost Effective Quality Control. New York: John Wiley & Sons, Inc. 1982.

The following specific examples are for the purpose of illustrating the invention and for exemplifying the specific nature thereof. It is to be understood, however, that this invention is not to be limited by and to these examples.

Determining the Foaming Properties of Surfactants

Foaming results from surfactants occupying the air/solution interface to stabilize films of solution that encircle air under agitation. Surfactants may produce more or less foam and contribute to higher or lower stability of these foams. This characteristic of a surfactant may be shown by shaking a tube in a controlled, repeatable fashion (generally through the use of automation) and then measuring the volume of foam in the tube relative to the volume of both foam and solution. Numerous examples of variations on this method may be found in scientific literature, such as Amaral, das Neves, J., Oliveira, Â. Z., and Bahia, M. F., "Foamability of Detergent Solutions Prepared with Different Types of Surfactants and Waters", Journal of Surfactants and Detergents, 11, 275-278 (2008).

EXAMPLES

Example 1: Monosodium Cyclohexylamine Dipropionate

Approximately 700 g of acrylic acid (obtained commercially from Sigma-Aldrich) was reacted with approximately 416 g of cyclohexylamine (obtained commercially from Sigma-Aldrich) for 6 hours under cooling with constant agitation at about 60-80° C. The resulting organic acid was neutralized in parts with aqueous sodium hydroxide over 2 hours under cooling with constant agitation at about 70° C. The neutralization was done to an extent that ensures that the partially neutralized acid is water soluble at room temperature. The reaction was performed in the presence of water such that the final water content was approximately 60 wt. %.

Example 2: Monosodium Butyloxypropylamine Dipropionate

Approximately 470 g of acrylic acid (obtained commercially from Sigma-Aldrich) was reacted with approximately 390 g of butyloxypropylamine for 6 hours under cooling with constant agitation at about 60-80° C. The resulting organic acid was neutralized with aqueous sodium hydroxide in parts over 2 hours under cooling with constant agitation at about 70° C. The neutralization was done to an extent that ensures that the partially neutralized acid is water soluble at room temperature. The reaction was performed in the presence of water such that the final water content was approximately 50 wt. %.

Example 3: 1.5 Sodium Butyloxypropylaminopropylamine Tripropionate

Approximately 232 g of acrylic acid (obtained commercially from Sigma-Aldrich) was reacted with approximately 192 g of n-butyloxypropylaminopropylamine for 6 hours under cooling with constant agitation at about 60-80° C. The resulting organic acid was neutralized in parts with aqueous sodium hydroxide over 2 hours under cooling with constant agitation at about 70° C. The neutralization was done to an extent that ensures that the partially neutralized acid is water soluble at room temperature. The reaction was performed in the presence of water such that the final water content was approximately 50 wt. %.

Example 4: Stability Exhibited by Monosodium Cyclohexylamine Dipropionate

Approximately 4 g of a 40 wt. % monosodium cyclohexylamine dipropionate solution was added to 200 g of 20 wt. % sodium hydroxide (15.5% total alkalinity expressed as $Na_2O$). This solution was heated to 150° C. and held at that temperature for 2 weeks. The aged sample was neutralized to a pH of 7 with hydrochloric acid and analyzed via liquid chromatography-mass spectorometry (LC-MS), using a Thermo Acclaim Surfactant Plus chromatography column. Mass spectrometric analyses were performed in positive electrospray ionization mode over the mass range of 100-2500 Daltons (Da) with a time of flight (TOF) mass spectrometer.

Figure 1:
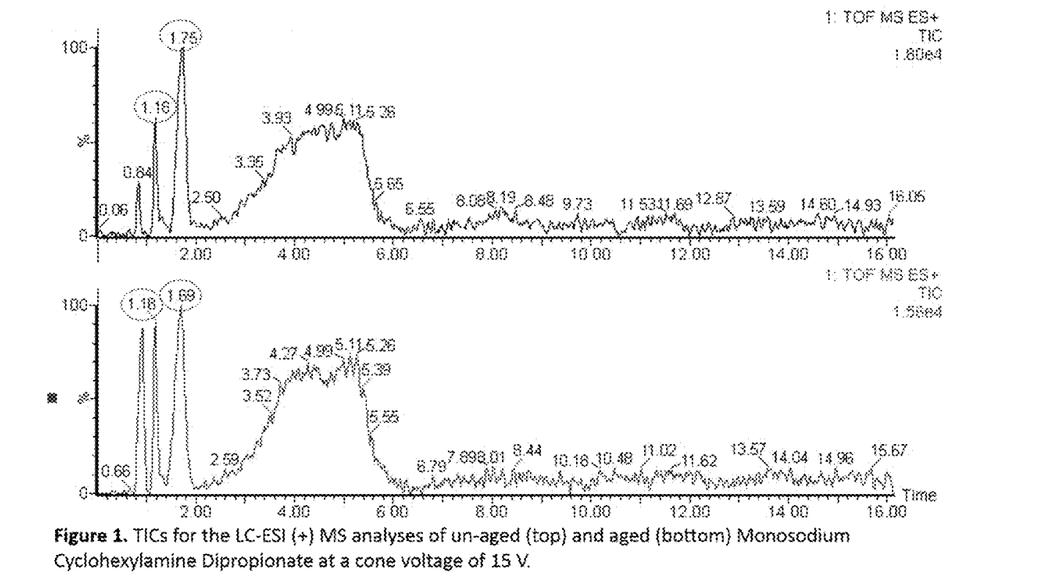
Figure 1. TICs for the LC-ESI (+) MS analyses of un-aged (top) and aged (bottom) Monosodium Cyclohexylamine Dipropionate at a cone voltage of 15 V.

The LC chromatograms for aged and un-aged amphoteric surfactant are shown in FIG. 1. The chromatographic peak at retention time 1.18 minutes was the same in both the aged and un-aged samples, and correlated to cyclohexylamine reacted with only one acrylic acid (m/z 172). For both samples, the mass spectra of the peak at retention time 1.7 minutes matched the expected [M+H]+ value of 244 for the structure of the surfactant.

The relative concentrations of the components to the rest of the peaks show that the surfactant maintained its molecular integrity through the aging process.

Example 5: Stability Exhibited By Monosodium Butyloxypropylamine Dipropionate

Approximately 4 g of a 40 wt. % monosodium butyloxypropylamine dipropionate solution was added to 200 g of 20 wt. % sodium hydroxide (15.5% total alkalinity expressed as $Na_2O$). This solution was heated to 150° C. and held at that temperature for 2 weeks. The aged sample was neutralized to a pH of 7 with hydrochloric acid and analyzed via liquid chromatography-mass spectorometry (LC-MS), using a Thermo Acclaim Surfactant Plus chromatography column. Mass spectrometric analyses were performed in positive electrospray ionization mode over the mass range of 100-2500 Daltons (Da) with a time of flight (TOF) mass spectrometer.

Figure 2:
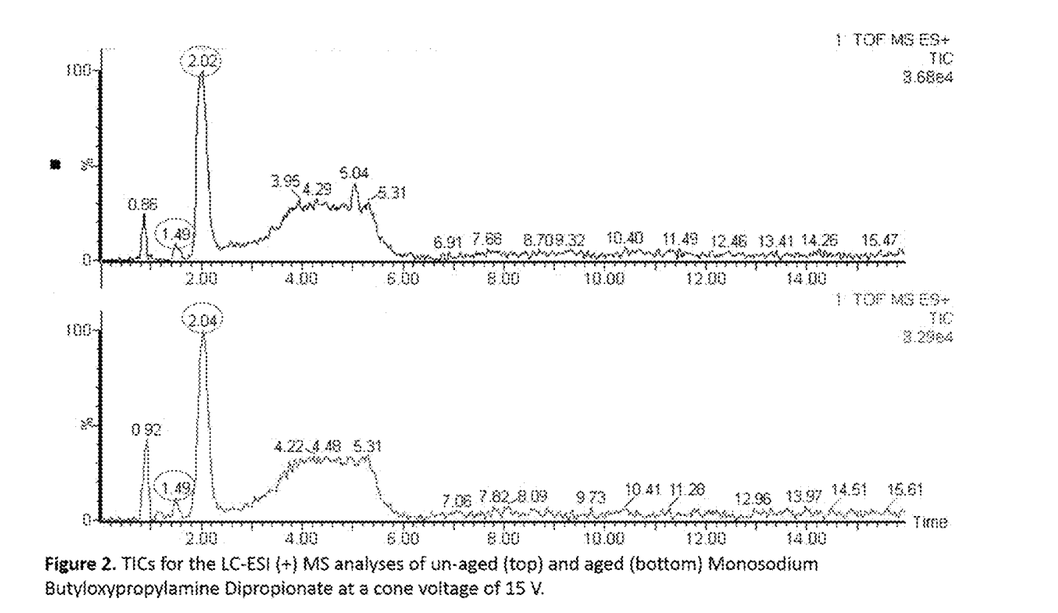
Figure 2. TICs for the LC-ESI (+) MS analyses of un-aged (top) and aged (bottom) Monosodium Butyloxypropylamine Dipropionate at a cone voltage of 15 V.

The LC chromatograms for aged and un-aged monosodium butyloxypropylamine dipropionate are shown in FIG. 2. The chromatographic peak at retention time 1.49 minutes was the same in both the aged and un-aged samples, and correlated to etheramine reacted with only one acrylic acid (m/z 204). The largest peak in both samples, at retention time 2.0 minutes matched the expected [M+H]+ for the structure of the expected product.

The relative concentrations of the components to the rest of the peaks show that the surfactant maintained its molecular integrity through the aging process.

Example 6: Surface Tension Reduction and Critical Micelle Concentration for Monosodium Cyclohexylamine Dipropionate (Ex 1) and Monosodium Butyloxypropylamine Dipropionate (Ex 2)

Monosodium Cyclohexylamine Dipropionate (Example 1) and Monosodium Butyloxypropylamine Dipropionate (Example 2) were examined to determine CMC in water and in 20% and 45% potassium hydroxide (KOH). These values and the equilibrium surface tensions (EST) at CMC are shown below in Table 1.

TABLE 1

Surface Tension Reduction and Critical Micelle Concentration for Example Surfactants

| Material | CMC (Wt %) | | | EST (mN/m) | | |
|---|---|---|---|---|---|---|
| | Water | 20% KOH | 45% KOH | Water | 20% KOH | 45% KOH |
| Monosodium Cyclohexylamine Dipropionate (Example 1) | 9.0 | 0.05 | 0.03 | 39.7 | 40.8 | 40.9 |
| Monosodium Butyloxypropylamine Dipropionate (Example 2) | 9.0 | 0.07 | 0.03 | 33.4 | 36.6 | 37.5 |

These values show that the claimed materials meet the definition of surfactants in that they will reduce surface tension and exhibit a critical micelle concentration.

Example 7: Foam Behavior for Example Surfactants

The foaming properties of solutions of Monosodium Cyclohexylamine Dipropionate (Example 1), Monosodium Butyloxypropylamine Dipropionate (Example 2), and 1.5 Sodium Butyloxypropylaminopropylamine Tripropionate (Example 3), prepared as 2 wt % in 45% KOH, were examined. Samples of each solution were shaken vigorously in an automated apparatus to ensure identical treatment of each sample and the volume of foam relative to the total volume of solution and foam was determined. Results of this examination are shown below in Table 2.

TABLE 2

Foaming Properties of Example Surfactants.

| Material | Foam Volume (as Percentage of Solution and Foam Volume) | | |
|---|---|---|---|
| | Initial | 1 Minute | 3 Minutes |
| Monosodium Cyclohexylamine Dipropionate (Example 1) | 25.6 | 12.3 | 0.0 |
| Monosodium Butyloxypropylamine Dipropionate (Example 2) | 53.3 | 48.1 | 32.1 |

TABLE 2-continued

Foaming Properties of Example Surfactants.

| Material | Foam Volume (as Percentage of Solution and Foam Volume) | | |
|---|---|---|---|
| | Initial | 1 Minute | 3 Minutes |
| 1.5 Sodium Butyloxypropylaminopropylamine Tripropionate (Example 3) | 57.6 | 57.5 | 53.1 |

It may be seen from this data that the claimed surfactants are capable of making both high and low foaming solutions.

Example 8: Dynamic Surface Tension of Monosodium Cyclohexylamine Dipropionate (Ex 1) and Monosodium Butyloxypropylamine Dipropionate (Ex 2)

Figure 3:
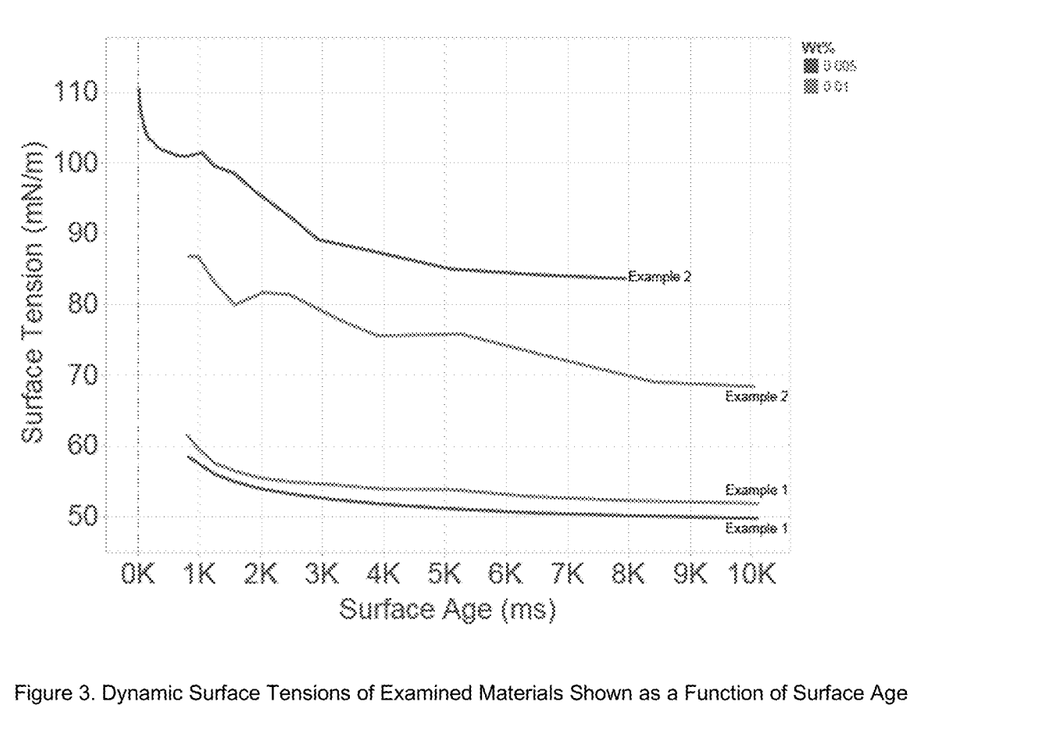
Figure 3. Dynamic Surface Tensions of Examined Materials Shown as a Function of Surface Age

Solutions of Monosodium Cyclohexylamine Dipropionate (Example 1) and Monosodium Butyloxypropylamine Dipropionate (Example 2) were prepared at concentrations of 0.01 wt % and 0.005 wt % in 45% KOH. A bubble tensiometer was employed to demonstrate the migration speed of these surfactants in the alkaline solution, revealed by the lowering of the solutions surface tension as a function of surface age. Results of this testing are shown below in FIG. 3.

The invention claimed is:
1. A cleaning solution, comprising:
a) one or more surfactant(s) according to Formula (I)

Formula (I)

wherein:
$R_1$ is a linear, branched, or cyclic, saturated or unsaturated aliphatic group having from 3 to 7 carbon atoms, or an aryl group having 6 or 7 carbon atoms or an alkylaryl group having 7 carbon atoms;
$R_2$ and $R_3$ may be identical or different and are bivalent alkyl radicals with two to four carbon atoms;
$R_4$, $R_5$, and $R_6$ may all be identical or two of them may be identical or all may be different and are selected from the group consisting of: ethyl group, 1-methylmethane group, n-propyl group, isopropyl group, n-butyl group, isobutyl group, and tert-butyl group;
$X_1$, $X_2$ and $X_3$ may all be identical or two of them may be identical or all may be different and are selected from the group consisting of: OH and O$^-$Y$^+$, wherein Y$^+$ is a cation;
wherein: m is 0 or 1, n is 0, 1, 2 or 3;
and wherein:
if m=0 and $R_1$ comprises a tertiary carbon atom attached to the nitrogen atom, then n is 1, 2 or 3;
if n=0 and m=0 or 1, then $R_1$ is selected from the group consisting of: a linear saturated aliphatic group having from 3 to 5 carbon atoms; a linear unsaturated aliphatic group having from 3 to 7 carbon atoms; a cyclic, saturated or unsaturated aliphatic group having from 3 to 7 carbon atoms; an aryl group having from 3 to 7 carbon atoms; and an alkylaryl group having from 3 to 7 carbon atoms;
b) one or more alkaline compound(s); and
c) water.

2. The cleaning composition of claim 1, wherein the one or more alkaline compounds of paragraph b) are present in an amount such that the total alkalinity of the cleaning solution, expressed as $Na_2O$ content, is 5 wt % or higher.

3. The cleaning solution of claim 2, wherein, if n=0 and m=0 or 1, $R_1$ is a linear aliphatic group having 3 or 4 carbon atoms.

4. The cleaning solution of claim 2, wherein, if n=0 and m=0 or 1, $R_1$ is a linear unsaturated aliphatic group having from 3 to 6 carbon atoms.

5. The cleaning solution of claim 2, wherein, if n=0 and m=0 or 1, $R_1$ is an aryl group or alkylaryl group having from 3 to 6 carbon atoms.

6. The cleaning solution of claim 2, wherein, if n=0 and m=0 or 1, $R_1$ is a cyclic, saturated or unsaturated aliphatic group having from 3 to 6 carbon atoms.

7. The cleaning solution of claim 2, wherein component b) is selected from the group consisting of: a metal hydroxide; an alkaline silicate; an alkaline phosphate; an amine; a chelating agent selected from the group consisting of: phosphates, carboxylates, phosphonates and polyphosphates; and mixtures of these compounds.

8. The cleaning solution of claim 2, wherein the composition does not include a hydrotroping agent.

9. The cleaning solution of claim 1, wherein component b) comprises at least one alkaline compound in an amount such that the total alkalinity of the cleaning solution, expressed as $Na_2O$ content, is 10 to 40 wt %.

10. The cleaning solution of claim 9, wherein component b) comprises one or more alkaline compound(s) selected from the group consisting of a strong base having a pKb value at 25° C. and 1 atm of below 1, and an alkaline silicate, or mixtures thereof, wherein the content of all silicates in sum in the overall composition is below 15% by wt.

11. The cleaning solution of claim 10, wherein component b) wherein the alkaline compound is selected from the group consisting of: sodium hydroxide; potassium hydroxide; potassium silicate; sodium silicate; and mixtures.

12. The cleaning solution of claim 9, wherein if n=0 and m=0 or 1, $R_1$ is selected from the group consisting of:
a) a linear aliphatic group having 3 or 4 carbon atoms; and
b) a linear unsaturated aliphatic group having from 3 to 6 carbon atoms.

13. The cleaning solution of claim 9, wherein if n=0 and m=0 or 1, $R_1$ is selected from the group consisting of:
a) a cyclic, saturated or unsaturated aliphatic group having from 3 to 6 carbon atoms; and
b) an aryl group or an alkylaryl group having from 3 to 6 carbon atoms.

14. The cleaning solution of claim 9, wherein the composition does not a hydrotroping agent.

15. A surfactant according to Formula (I):

$$R_1-(O-R_2)_m-N(R_5-COX_1)-(R_3-N)_n-(R_4)-COX_2$$
$$|$$
$$(R_6)-COX_3$$

Formula (I)

wherein:
$R_1$ is a linear, branched, or cyclic, saturated or unsaturated aliphatic group having from 3 to 7 carbon atoms, or an aryl group having 6 or 7 carbon atoms or an alkylaryl group having 7 carbon atoms;
$R_2$ and $R_3$ may be identical or different and are bivalent alkyl radicals with two to four carbon atoms;
$R_4$, $R_5$, and $R_6$ may all be identical or two of them may be identical or all may be different and are selected from the group consisting of: an ethyl group, 1-methylmethane group, n-propyl group, isopropyl group, n-butyl group, isobutyl group, and tert-butyl group;
$X_1$, $X_2$ and $X_3$ may all be identical or two of them may be identical or all may be different and are selected from the group consisting of: OH and $O^-Y^+$, wherein $Y^+$ is a cation;
m is 0 or 1, n is 0, 1, 2 or 3,
wherein: m is 0 or 1, n is 0, 1, 2 or 3,
and wherein
if m=0 and $R_1$ comprises a tertiary carbon atom attached to the nitrogen atom, then n is 1, 2 or 3;
if n=0 and m=0 or 1, then $R_1$ is selected from the group consisting of: a linear saturated aliphatic group having from 3 to 5 carbon atoms; a linear unsaturated aliphatic group having from 3 to 7 carbon atoms; a cyclic, saturated or unsaturated aliphatic group having from 3 to 7 carbon atoms; an aryl group having from 3 to 7 carbon atoms; and an alkylaryl group having from 3 to 7 carbon atoms;
if n=1 and m=0, then either $R_3$ is a bivalent alkyl with 3 or 4 carbon atoms or $R_1$ is a linear or branched unsaturated aliphatic group having from 3 to 7 carbon atoms, a cyclic, saturated or unsaturated aliphatic group having from 3 to 7 carbon atoms, an aryl group having from 3 to 7 carbon atoms, or an alkylaryl group having from 3 to 7 carbon atoms.

16. The surfactant of claim 15, wherein, if n=0 and m=0 or 1, $R_1$ is a linear aliphatic group having 3 or 4 carbon atoms.

17. The surfactant of claim 15, wherein, if n=0 and m=0 or 1, $R_1$ is a linear unsaturated aliphatic group having from 3 to 6 carbon atoms.

18. The surfactant of claim 15, wherein, if n=0 and m=0 or 1, $R_1$ is an aryl group or an alkylaryl group having from 3 to 6 carbon atoms.

19. The surfactant of claim 15, wherein, if n=0 and m=0 or 1, $R_1$ is a cyclic, saturated or unsaturated aliphatic group having from 3 to 6 carbon atoms.

* * * * *